United States Patent
Martín et al.

(10) Patent No.: US 6,352,720 B1
(45) Date of Patent: *Mar. 5, 2002

(54) PHARMACEUTICAL FORMULATIONS COMPRISED OF COMPACTED AMOXICILLIN GRANULATES

(75) Inventors: Luis Carvajal Martín; Juan Dedios Romero, both of Toledo (ES)

(73) Assignee: Laboratorios Beecham SA, Madrid (ES)

(*) Notice: Subject to any disclaimer, the term of this patent is extended or adjusted under 35 U.S.C. 154(b) by 0 days.

This patent is subject to a terminal disclaimer.

(21) Appl. No.: 09/645,001

(22) Filed: Aug. 24, 2000

Related U.S. Application Data

(62) Division of application No. 09/217,304, filed on Dec. 21, 1998, now Pat. No. 6,110,497, which is a division of application No. 08/729,222, filed on Oct. 9, 1996, now Pat. No. 5,851,550, which is a continuation of application No. 08/146,069, filed as application No. PCT/EP92/01024 on May 2, 1992, now abandoned.

(30) Foreign Application Priority Data

May 8, 1991 (GB) .............................. 9109862

(51) Int. Cl.⁷ ................................. A61K 9/20
(52) U.S. Cl. .................. 424/464; 424/465; 514/772.3; 514/775; 514/777; 514/778; 514/779; 514/781
(58) Field of Search ................................ 424/464, 465, 424/489, 470, 469

(56) References Cited

U.S. PATENT DOCUMENTS

| | | | |
|---|---|---|---|
| 4,950,484 A | 8/1990 | Olthoff et al. | 424/464 |
| 5,275,823 A | 1/1994 | France et al. | 424/489 |
| 5,851,550 A | * 12/1998 | Martin et al. | 424/464 |
| 6,110,497 A | * 8/2000 | Martin et al. | 424/464 |

FOREIGN PATENT DOCUMENTS

| | | | |
|---|---|---|---|
| CA | 1199871 | | 1/1986 |
| EP | 0281200 | | 9/1988 |
| FR | 2320731 | * | 3/1977 |
| GB | 2005538 | | 4/1979 |

* cited by examiner

Primary Examiner—James M. Spear
(74) Attorney, Agent, or Firm—Dara L. Dinner; Stephen Venetianer; Charles M. Kinzig

(57) ABSTRACT

The present invention discloses tablet formulations, produced by dry roller compaction comprising compacted granulates of a mixture of a medicament and an intragranular disintegrant. The granulates are compacted together into a tablet with an extra-granular disintegrant, an optional extragranular lubricant and excipients.

11 Claims, No Drawings

PHARMACEUTICAL FORMULATIONS COMPRISED OF COMPACTED AMOXICILLIN GRANULATES

This application is a divisional of U.S. Ser. No. 09/217,304, filed Dec. 21, 1998, now U.S. Pat. No. 6,110,497, which is a divisional application of U.S. Ser. No. 08/729,222, filed Oct. 9, 1996, now U.S. Pat. No. 5,851,550, which is a continuation of U.S. Ser. No. 08/146,069, filed Jul. 14, 1994, abandoned, which is the §371 national stage entry of PCT/EP92/01024, filed May 2, 1992.

The present invention relates to pharmaceutical formulations for oral administration in the treatment of bacterial infections, and to processes for the manufacture of such formulations.

It is known to provide formulations for oral administration in the form of water-dispersible granules or tablets which may be swallowed or dispersed in water prior to swallowing.

In one known method of tablet manufacture, an intermediate granulate is prepared comprising an intragranular disintegrant and an active material such as an antibiotic. This granulate is then mixed with an intergranular disintegrant (and optional other additives including a lubricant) and compressed into tablets. Such a process, tablets and granulate are for example described in EP 0281200A, CA 1199871 and JP 3240023A.

It is desirable that such solid formulations should rapidly disperse on immersion in water, for example by rapid disintegration of tablets.

Novel formulations have now been discovered which assist in achieving some of the above-mentioned desirable features.

The invention therefore provides a tablet formulation having a structure comprising compacted granulates; the granulates comprising at least one compacted medicament optionally together with an intra-granular disintegrant; the granulates being compacted together into a tablet form together with an extra-granular disintegrant and optionally also together with an extra-granular lubricant, provided that if a lubricant is present the amount of lubricant is less than 0.5% by weight of the total tablet.

In the tablets of this invention the granulates may be in a crushed state resulting from the compaction of the tablet, and consequently may not have discrete boundaries, or may be sub-divided or broken up into smaller granulates. The invention is intended to include tablets having such a structure containing crushed granulates. Preferably the size of the granulates is in the range 100 $\mu$m to 2 mm, suitably around 1 mm±0.25 mm, maximum dimension.

The medicament is preferably one which is capable of oral absorption, in particular β-lactam antibiotics optionally in combination with a β-lactamase inhibitor. A preferred antibiotic is amoxycillin, for example present as a hydrate such as the trihydrate. Amoxycillin may be used alone, or may optionally be used in combination with other β-lactam antibiotics and/or β-lactamase inhibitors such as clavulanic acid or salts (especially the potassium salt) thereof, for example in a weight ratio equivalent to amoxycillin: clavulanic acid in the range 12:1 to 1:1 such as around 4:1 or 2:1. Preferably the proportion of the antibiotic in the tablet is 60–98% by weight of the total tablet, in the case of amoxycillin trihydrate calculated as the weight of the trihydrate. Preferably the particles of antibiotic in the granulates are in the size range 1 $\mu$m to 300 $\mu$m, especially 10 $\mu$m to 200 $\mu$m. A typical suitable size distribution of the antibiotic particles is: >200$\mu$ 5% or less, 200–100$\mu$ 5–15%, 100–50$\mu$ 7.5–15%, <50$\mu$ 70% or more.

Suitable intra-granular disintegrants are starches, such as maize starch and rice starch, cross-linked N-vinyl-2-pyrrolidone ("CLPVP"), sodium starch glycollate, croscarmellose sodium and formaldehyde—casein, or combinations thereof. A preferred intra-granular disintegrant is CLPVP, for example as marketed under the trade names Polyplasdone XL and Polyplasdone XL-10.

The granulate may consist entirely of antibiotic(s), optionally in the case of a β-lactam antibiotic combined with a β-lactamase inhibitor, and an intra-granular disintegrant. Alternatively, particularly when the granulate contains clavulanic acid or a salt thereof, the granulate may also contain a diluent such as silica gel (eg Syloid-Trade Mark). Suitable intra-granular disintegrants for use with antibiotics are CLPVP and sodium starch glycollate. Typically the proportion of intra-granular disintegrant in the granulate may be 0.1–10 wt % of the granulate, suitably 1.0–8.0 wt %, such as 1.25–3.5 wt %. Typically the proportion of an antibiotic or antibiotic+β-lactamase inhibitor combination in the granulate may be 99.9–90 wt %, suitably 99–92 wt %, e.g. 99–95 wt %, such as 98.75–96.5 wt % of the weight of the granulate. When the granulate contains a diluent, this may comprise up to 30 wt % of the granulate, but is conveniently present in a 1:1 weight ratio with the amount of clavulanic acid or its salt in the granulate. When the granulate contains a diluent the granulate will contain a correspondingly lower proportion of antibiotic or antibiotic+β-lactamase inhibitor combination, for example 70–99.9 wt % of the granulate.

The intimate contact between the antibiotic and the intra-granular disintegrant in the granulate appears to assist in improved disintegration and dispersion of the granulate in contact with water to release antibiotic particles in the size range referred to above, and to provide finely dispersed suspensions. Problems are associated with preparation of granulates which include clavulanic acid or its salts, due to their hygroscopicity, and the granulate of the invention facilitates manufacture.

In the tablet formulation the granulate may suitably comprise 70% or more, e.g. 80% or more, 90% or more or 95% or more of the total tablet weight so that a high proportion of medicament is present.

The extra-granular disintegrant may be a conventional disintegrant for example starches such as maize-starch and rice starch, CLPVP, sodium starch glycollate, croscarmellose sodium, microcrystalline or microfine cellulose, low-substituted hydroxypropylcellulose (i.e. cellulose partially substituted with 2-hydroxypropyl groups, e.g. less than 25% substituted, preferably 7–16% substituted), cross-linked sodium carboxymethylcellulose, swellable ion exchange resins, formaldehyde-casein, or alginates. Preferred extra-granular disintegrants are CLPVP, sodium starch glycollate, microfine cellulose and croscarmellose sodium, and combinations thereof. An example of an extra-granular disintegrant combination is a combination of microcrystalline or microfine cellulose with sodium starch glycollate, croscarmellose sodium, or CLPVP, containing 80–90% by weight cellulose.

The proportion of extra-granular disintegrant to total tablet weight may vary between broad limits, for example 0.1–25 weight %. For example if CLPVP or sodium starch glycollate is used as extra-granular disintegrant it may suitably be used as such in a proportion 0.1–5.0 weight %, suitably 0.1–3.0 weight %, preferably 0.1–1.5 weight % of the total tablet weight. If cellulose or a combination containing cellulose is used, e.g. as described above containing around 80–90% by weight of cellulose, the extra-granular disintegrant may comprise 1–25 weight %, typically around 1–20 weight % of the total tablet.

Suitable lubricants are those conventional to the art, such as long-chain fatty acids, such as stearic acid, or salts thereof, in particular Group II metal salts, such as of magnesium or calcium.

A preferred lubricant is magnesium stearate. It is preferred to use a lubricant proportion as low is possible e.g. 0.35% by weight or preferably lower, e.g. 0.275% or less, e.g. 0.25% or less, preferably using no lubricant at all.

The granulate may also contain an intra-granular lubricant, which may be selected from the same materials as the extra-granular lubricant, such as magnesium stearate. However an advantage of the present tablet formulation is that the granulate and tablet need not contain any lubricant. This can lead to improved wettability and hence improved disintegration of the tablet. Further a reduced lubricant proportion can lead to a lower tablet weight for a given dose of antibiotic and in the case of dispersible formulations can avoid the "smeared" appearance associated with higher lubricant proportions.

The tablet may also include conventional excipients, typically present up to about 10% of the total tablet weight. These may include flavouring agents, for example flavourings such as menthol, peppermint, vanilla or fruit flavourings, flavouring agents typically being present up to around 0.5–5% by weight of the whole tablet, and sweeteners, e.g. aspartame, present of up to around 15 mg per unit dose. Excipients may also include colouring agents, preservatives, suspending aids and fillers such as silicon dioxide, microcrystalline cellulose, dicalcium phosphate, lactose, sorbitol, calcium carbonate or magnesium carbonate. Such excipients are preferably mixed with the extra-granular disintegrant and lubricant (if present). The materials present in the tablets should have low free moisture content and preferably be pre-dried. In some cases, particularly when the medicament is an antibiotic, and includes clavulanic acid or its salts, it may be necessary to include a dessiccant diluent such as silica gel as an excipient, in a proportion of about 1–5% of the weight of the antibiotic, mixed with the antibiotic and intra-granular disintegrant in the granulates. The particle size of the excipients does not appear to be critical but it is desirable to exclude agglomerates.

The tablet may also contain an effervescent couple of known type, e.g. a solid acid and an alkali metal carbonate or bicarbonate which generates carbon dioxide on contact with water to assist in disintegration of the tablet.

The tablets may be film coated in a conventional manner, e.g. for cosmetic, palatability or production purposes. Suitable coatings include hydroxypropylcellulose, acrylate and/ or methacrylate co-polymers, resins etc. Alternatively the coating may be an enteric coating, e.g. which is insoluble in acidic gastric juice but soluble in alkaline digestive juice. Such a coating enables the antibiotic to pass through the stomach into the duodenum, from where it is absorbed. Suitable enteric coatings include cellulose acetate phthalate.

Preferred combinations of components for the tablets of this aspect of the invention therefore comprise:

| Component | wt % | Example |
|---|---|---|
| Granulate: | | |
| Medicament | 70–99 | Amoxycillin ± Pot.clavulanate |
| Disintegrant | 0.1–4 | CLPVP, Microcryst. cellulose, sodium starch glycollate |
| Diluent | 0–30 | Silica gel |
| Tablet: | | |
| Granulate | 70+ | above |
| Disintegrant | 0.1–25 | CLPVP, Microcryst. cellulose, sodium starch glycollate. |
| Lubricant | 0–0.35 | Magnesium stearate |
| Excipients | to 100 | Aspartame, flavour, colour, silicon dioxide |

The invention also provides a process for the manufacture of a tablet in which granulates comprising a compacted mixture of at least one medicament such as a β-lactam antibiotic either alone or in combination with a β-lactamase inhibitor, together with an intra-granular disintegrant are mixed with an extra-granular disintegrant and optionally with an extra-granular lubricant and optionally with any excipients, provided that if a lubricant is present it amounts to less than 0.5% by weight of the mixture, and the mixture is compressed into tablets.

Suitable and preferred antibiotics, intra- and extra-granular disintegrants, lubricants, excipients, granulate and particle sizes, and relative proportions thereof are as discussed above.

The necessary granulate for the process of this aspect of the invention may be made in a further process by mixing the medicament in a powdered form with the intra-granular disintegrant in a dry state, and compacting the mixture under pressure. Insofar as this further process uses as intra-granular disintegrant CLPVP, sodium starch glycollate, casein-formaldehyde, croscarmellose sodium or combinations thereof, it is believed to be novel, and is a further aspect of this invention.

In this further process, it is desirable to mill and sieve the antibiotic to achieve the desired particle size range. It is also desirable to mill and sieve intra-granular disintegrant to a suitable particle size, for example in the case of CLPVP about 30µ, but particle size does not appear to be critical.

The compaction of the mixture into granulates may be by conventional dry compaction means, for example pressing, rolling, slugging extrusion etc, and a suitable pressure for the compaction process is 30–200 KN, e.g. 35–65 KN preferably 40–50 KN. The above-described granulate formulations are particularly suited to formation by roller compaction. It may be necessary to mill and sieve the compacted mixture after compaction so as to achieve a suitable size fraction of the granulate. Compression into tablets may be carried out in a conventional manner, e.g. on a conventional tabletting machine. As an optional further step the tablets may be coated as described above.

When the granulates described above contain as a medicament a β-lactam antibiotic such as amoxycillin together in combination with a β-lactamase inhibitor such as clavulanic acid or its salts (especially potassium clavulanate) these granulates are believed to be novel and are a further aspect of this invention. Suitable and preferred features of these granules are as discussed above.

The granulates described above may be suitable for use in the preparation of other pharmaceutical formulations in addition to tablets, for example they may be supplied as a free-flowing granulated formulation in sachets containing a suitable unit dose. This may also for example be dissolved in water together with excipients such as sweetening agents, thickeners, preservatives and buffers such as sodium benzoate, sodium acetate and sodium citrate to form a syrup fonniulabinn, for example for administration to small children.

The ability of the granulates to form a loose compact, and their rapid dispersion in contact with water makes them particularly suitable for use in encapsulated formulations. Therefore in a further aspect of this invention there is provided an encapsulated formulation comprising such granulates. The encapsulated formulation may optionally include an extra-granular lubricant, which if present is suitably in an amount of less than 0.5% by weight of the granulates, being contained within a pharmaceutical capsule.

The medicament is preferably one which is capable of oral absorption, in particular a β-lactam antibiotic optionally in combination with a β-lactamase inhibitor. Suitable and preferred antibiotics, β-lactamase inhibitors, intra-granular disintegrant, extra-granular lubricant, granulate and particle sizes, and relative proportions thereof for a capsule formulation are as discussed above, except that a preferred proportion of lubricant is 0.1–0.5%, particularly 0.32–0.35% by weight of the granulate.

The pharmaceutical capsule may be an entirely conventional capsule, capable of dissolving in the stomach to release its contents, for example made of gelatine.

The formulations described above preferably contain unit doses of antibiotic, for example 375, 500, 750 or 1000 mg of amoxycillin per tablet or capsule. The tablets may be dispersed in water prior to ingestion, or may alternatively be chewed or swallowed whole.

The invention further provides a pharmaceutical formulation as described above, for use as an active therapeutic substance.

The invention further provides a pharmaceutical formulation as described above, in which the medicament is a β-lactam antibiotic optionally in combination with a β-lactamase inhibitor, for use in the treatment of bacterial infections.

The invention futher provides a method of use of a pharmaceutical formulation as described above in which the medicament is a β-lactam antibiotic optionally in combination with a β-lactamase inhibitor in the manufacture of a medicament for use in the treatment of bacterial infections.

The invention further provides a method of treament of bacterial infections in mammals which comprises the administration to the mammal of an effective amount of a pharmaceutical formulation as described above, in which the medicament is a β-lactam antibiotic, optionally in combination with a β-lactamase inhibitor.

The invention will now be described by way of example only.

EXAMPLE 1

Granulate

Amoxycillin trihydrate was milled and sieved using an 0.04 or 0.027 inch (1.0–0.7 mm) aperture sieve, and was mixed for 15 minutes in a blender with dried cross-linked polyvinylpyrrolidone having a molecular weight of approximately 1 million and a density of 1.22 mg/cm 3 (polyplasdone XL-Trade Mark), the mixture containing 3.4% of CLPVP by weight.

The mixture was consolidated using a roller compacter at a controlled pressure of 50 KN. The compacted flakes were granulated in a mill, or granulated through a sieve fitted with a 1mm mesh to obtain a suitable size fraction.

EXAMPLE 2

Tablet

Tablets were prepared having the composition below;

| Component | Weight mg. | Weight % | |
|---|---|---|---|
| Amoxycillin trihydrate | 750[1] | 78.95 | as granulate of example 1 |
| CLPVP | 26.0 | 2.73 | |
| Sodium Starch Glycollate (Primogel) | 21.6 | 2.27 | |
| Magnesium Stearate | 2.0 | 0.21 | |
| Aspartame | 20.0 | 2.10 | extra granulate |
| Microcrystalline Cellulose (Avicel PH102) | 130.4 | 13.74 | |

[1]Expressed or free acid equivalent: To prepare these tablets, the dried sodium starch glycollate, magnesium stearate and microcrystalline cellulose were sieved, then blended with the granulate of example 1. The aspartame was then added, and this mixture was then blended until homogenous (5 minutes). The mixture was then compressed into tablets on a conventional tabletting machine.

EXAMPLE 3

Granulate

A granulate was prepared using a procedure identical to example 1, comprising 97 weight % of amoxycillin trihydrate and 3 weight % polyplasdone XL, and using a controlled pressure of 40–50 KN.

EXAMPLE 4

Tablet

Tablets were prepared having the composition below:

| Component | wt. mg | wt. mg | wt. mg | wt. mg | wt. % |
|---|---|---|---|---|---|
| Amoxycillin | 375 | 500 | 750 | 1000 | 83.00[1] |
| CLPVP | 17.5 | 23.33 | 35 | 46.65 | 3.78[2] |
| Peppermint dry flavour | 3 | 4 | 6 | 7.99 | 0.65 |
| Aspartame | 7.5 | 10 | 15 | 19.99 | 1.62 |
| Magnesium stearate | 1 | 1.34 | 2 | 2.67 | 0.21 |

[1]As 95 wt. % of amoxycillin trihydrate.
[2]3% as intra-granular, and 0.78% as extra-granular disintegrant.

To prepare these tablets, the dried flavour, aspartame, magnesium stearate and a weight of CLPVP (polyplasdone XL) corresponding to 0.78 wt. % of the total weight of the mixture was mixed for 5 minutes with the granulate of example 3 to give the wt % indicated above. The mixture was then compressed into tablets on a conventional tabletting machine.

Typical tablets of this example containing 750 mg of amoxycillin as the trihydrate had the following characteristics:

| | |
|---|---|
| weight: | 925 mg ± 5% |
| hardness: | >16 KP |
| time of dispersal: in water | <1 minute |
| friability: | <1% |
| presentation: | Oval, 17 × 10 × 7 mm tablets |

EXAMPLE 5

Granulate

A granulate was prepared using a procedure identical to that of example 1, comprising 97.12 weight % amoxycillin trihydrate together with 2.88 weight % sodium starch glycollate (as "Primogel") as intra-granular disintegrant.

EXAMPLE 6

Tablet

Tablets were prepared having the composition below:

| Component % | Weight mg. | Weight % | |
|---|---|---|---|
| Amoxycillin | 750 mg[1] | 78.95 | as granulate |
| Sodium starch glycollate | 21.6 mg | 2.27 | of example 5 |
| Magnesium stearate | 2.0 mg | 0.21 | |
| Dried microcrystalline cellulose (Avicel PH102) | to 950 mg | 18.57 | extra granulate |

[1]As free acid equivalent

To prepare these tablets, the granulate of example 5 was sieved using a 1mm sieve, and was then blended with appropriate quantities of the magnesium stearate (lubricant) and microcrystalline cellulose, mixing for 15 minutes. The mixture was then compacted to form tablets having the following characteristics:

| weight: | 950 mg |
|---|---|
| hardness: | 12–16 KP |
| time of dispersal: | 10–15 seconds (37° C.), |
| in water | 20–25 seconds (20° C.) |

These tablets could be provided in the above-described uncoated state for dispersion in water prior to swallowing, or could be film coated for swallowing.

EXAMPLE 7

Encapsulated Formulation

The granulate of example 3 was made up into a loose compact under gentle pressure together with an amount of magnesium stearate lubricant to total 0.34% by weight of the total compact. This loose compact was sealed into gelatin capsules containing the following mixture:

| Component | Weight mg. | Weight % |
|---|---|---|
| Amoxycillin trihydrate: | 573.91[1] | 96.8 |
| CLPVP: | 17 | 2.9 |
| magnesium stearate: | 2 | 0.34 |

[1]corresponds to 500 mg amoxycillin free acid

EXAMPLE 8

Sachet Formulation

| Component | Weight mg. | Weight % | |
|---|---|---|---|
| Amoxycillin trihydrate Potassium clavulanate/syloid AL-1 blend 1:1 | 2711.1 | 76.12 | granulate |
| Polyplasdone XL dried | | | |
| Polyplasdone XL dried | 13.5 | 0.38 | |
| Lemon dry flavour | 408.0 | 11.45 | |
| Strawberry dry flavour | 132.0 | 3.71 | |
| Peach dry flavour | 102.0 | 2.86 | extra granular |
| Aspartame | 45.0 | 1.26 | |
| Xantham Gum | 150.0 | 4.21 | |

Granules were in a manner identical to that of example 1, i.e. by milling and sieving of the granulate components, followed by roller compaction (50 KN) and granulation. The granules could be made up into a mixture suitable for a sachet presentation with the extra-granular excipients.

The granulate of this example could be supplied confining appropriate weights of amoxycillin/clavulanate in a sachet, and is also suitable for making up into syrup formulations. For example the weights listed may be made up into 60 ml to produce a 156.25 mg/5 ml syrup or double the listed weights may be made up into 60 ml to produce a 312.5 mg0.5 ml syrup. These syrups do not contain any added sugar.

EXAMPLE 9

Granulate

| Component | Weight mg. | Weight % | |
|---|---|---|---|
| Amoxycillin trihydrate | 581.4[1] | 64.0 | |
| Potassium clavulanate | 152.4[2] | 16.8 | |
| Syloid AL-1 | 152.4 | 16.8 | as granulate |
| Polyplasdone XL dried | 22.0 | 2.42 | |

[1]corresponds to 500 mg amoxycillin free acid.
[2]corresponds to 125 mg free clavulanic acid.

Granules are prepared using this mixture in a manner identical to that of example 8. These granules are suitable for supply in a sachet, together with flavour and sucrose in the proportions listed below for the quantity of granules listed above per sachet:

| Lemon dry flavour | 136.0 mg |
|---|---|
| Strawberry dry flavour | 44.0 mg |
| Peach dry flavour | 34.0 mg |
| Sucrose | to 3500 mg |

Sachets containing other weights of amoxycillin, e.g. 250 or 125 mg could be made up using proportional amounts of the weights listed and made up to 1750 mg total weight with sucrose.

EXAMPLE 10

Tablet

| Component | Weight mg. | Weight % | |
|---|---|---|---|
| Amoxycillin trihydrate | 581.4[1] | 61.2 | |
| Potassium clavulanate | 152.4[2] | 16.0 | |
| Syloid AL-1 | 152.4 | 16.0 | as granulate |
| Polyplasdone XL dried | 17.4 | 1.83 | |
| Dry flavour (Peppermint or mandarin) | 6.0 | 0.63 | |
| Polyplasdone XL dried | 25.0 | 2.63 | |
| Aspartame | 15.0 | 1.58 | extra granulate |
| Colouring | 5.0 | 0.53 | |
| Magnesium stearate | 2.5 | 0.26 | |

[1]corresponds to 500 mg amoxycillin free acid.
[2]corresponds to 125 mg free clavulanic acid.

Granules are prepared using this mixture in a manner identical to that of example 8. The flavour, polyplasdone XL, colouring and magnesium stearate were sieved then blended with the granulate. The aspartame was then added, and this mixture was then compressed into tablets on a conventional tabletting machine. This tablet contains 625.0 mg of the amoxycillin: clavulanate combination, and the quantities used may be halved to prepare a tablet containing 312.5 mg.

EXAMPLE 11
Tablet

| Component | Weight mg. | Weight % | |
|---|---|---|---|
| Amoxyciliin trihydrate | 290.7[1] | 46.3 | as granulate |
| Potassium clavulanate | 152.4[2] | 24.3 | |
| Syloid AL-1 | 152.4 | 24.3 | |
| Polyplasdone XL dried | 8.7 | 1.38 | |
| Dry flavour (Peppermint or mandarin) | 3.0 | 0.48 | extra granulate |
| Polyplasdone XL dried | 12.5 | 2.00 | |
| Aspartame | 7.5 | 1.19 | |
| Colouring | 2.5 | 0.39 | |
| Magnesium stearate | 1.25 | 0.20 | |

[1] corresponds to 250 mg amoxycillin free acid.
[2] corresponds to 125 mg free clavulanic acid.

Tablets were made from this mixture using a procedure identical to that of example 10.

EXAMPLE 12
Sachet or Syrup Formulations

| Component | | Weight mg | w + % |
|---|---|---|---|
| Amoxycillin:potassium clavulanate 4:1 w:w + 3 wt % CLPVP | granulate[1] | 2255.6 | 63.3 |
| CLPVP | | 13.5 | 0.38 |
| Lemon dry flavour | | 408.0 | 11.46 |
| Strawberry dry flavour | | 132.0 | 3.71 |
| Peach dry flavour | | 102.0 | 2.86 |
| Silicon dioxide USNF (Syloid AL-1) | | 450.0 | 12.64 |
| Aspartame | | 45.0 | 1.26 |
| Xantham gum | | 150.0 | 4.21 |
| Total weight | | 3561.6 | 100.0 |

[1] amox: clav expressed as free acid.

The granulate was prepared using the procedure of example 8. This formulation could be supplied in a sachet, or could be made up into a syrup, for example at concentrations of 3561.6 mg/60 ml or 7123.2 mg/60 ml or 7123.2 mg/60 ml (=156.25 and 312.5 mg amoxycillin: clavulanate/5 ml respectively). To adjust the syrup to a suitable viscosity and pH, aerosil 200, succinic acid and/or methocel E-15 (dry) may be used.

EXAMPLE 13
Sachet Formulation

| Component | | Weight (mg) | | | w + % |
|---|---|---|---|---|---|
| Granulate (Amox:Kclav 4:1 or 7:1 + 3% PVP) | 500 | 250 | 125 | 875 | 7–25 |
| Lemon dry flavour | 136 | 68 | 34 | 136) | |
| Strawberry dry flavour | 44 | 22 | 11 | 44) | 3–6.1 |
| Peach dry flavour | 34 | 17 | 8.5 | 34) | |
| Silicon Dioxide U.S.N.F. | 150 | 75 | 37.5 | 150 | 2.1–4.3 |
| (Syloid AL-1) | | | | | |
| Sucrose to | 3500 | 1750 | 1750 | 3500 | to 100 |

(1) weights and Amox/Kclav expressed as free acid.

The granulate was prepared using the procedure of example 8, and was then mixed with the other excipients.

EXAMPLE 14
Tablet Formulation

| Amox: clav[1] Component | 4:1 | 4:1 | 2:1 | 7:1 | w + % |
|---|---|---|---|---|---|
| | weight (mg) | | | | |
| Granulate 2 | 751.9 | 376.0 | 452.1 | 1201.3 | 70.90 |
| Dry Flavour 3 | 6.0 | 3.0 | 3.0 | 8.0 | 0.48–0.63 |
| Poliplasdone XL dried | 100.0 | 50.0 | 66.5 | 110.0 | 8.1–10.7 |
| Aspartame | 15.0 | 7.5 | 7.5 | 15.0 | 1.1–1.6 |
| Colouring | 4–5 | 2–2.5 | 2–2.5 | 4–5 | 0.3–0.55 |
| Mag. Stearate | 2.5 | 1.25 | 1.25 | 3.4 | 0.19–0.26 |
| Silicon Dioxide Syloid AL-1 to | 950 | 475 | 628 | 1350 | to 100 |

(1) Amox: clav expressed as weight: weight of amoxycillin: clavulanate free acid.
(2) Granulate = amox: clav + 3% CLPVP.
(3) Peppermint or mandarin.

The granulate was prepared using the procedure of example 9.

The granulate was prepared using the procedure of example 9. The other excipients except aspartame were sieved and blended then mixed with the granulate. The aspartame was then added, and this mixture was then compressed into tablets in a conventional tabletting machine. This tablet contained 625 mg of the amoxycillin:clavulante blend. Tablets of different strengths could be formulated correspondingly, eg containing 1000, 375 or 312.5 mg of the amoxycillin:clavulanate combination.

EXAMPLE 15
Tablet Formulation

| Component | Weight (mg) | | | | w + % |
|---|---|---|---|---|---|
| Granulate (Amox.Kclav) 4:1 or 7:1 + 3% PVP | 751.9 | 376.0 | 188.0 | 1201.3 | 71–83 |
| Magnesium stearate Ph. Eur | 2.6 | 1.3 | 0.65 | 3.9 | 0.25–0.27 |
| Silicon Dioxide USP/NF (Syloid AL-1) | 44.0 | 22.0 | 11.0 | 44.0 | 3–4.25 |
| Microcrystalline cellulose Avicel pH 112 dried . . . to | 850.0 | 425.0 | 212.5 | 1275.0 | 1.8–5 |
| Organic film coating | yes | yes | yes | yes | to 100 |
| Actual weight | 1050.0 | — | — | 1450.0 | |

(1) amox: clav expressed as free acid.

The tablet was made up in a manner identical to that of example 14.

The weights and relative proportions of the components of examples 1 to 15 could be varied about the figures listed, but suitably are within ±10% of those listed, desirably within ±5%, especially ±2.5%.

What is claimed is:

1. A tablet formulation having a structure comprising compacted granulates; the granulates comprising amoxicillin optionally together with an intra-granular disintegrant; the granulates being compacted together into a tablet form together with an extra-granular disintegrant and optionally also together with an extra-granular lubricant, provided that if a lubricant is present the amount of lubricant is less than 0.5% by weight of the total tablet.

2. A tablet formulation according to claim 1 wherein the intra-granular disintegrant is selected from the group consisting of maize starch, rice starch, cross linked N-vinyl-2-pyrrolidone ("CLPVP"), sodium starch glycollate, croscarmellose sodium, formaldehyde-casein and combinations thereof.

3. A tablet formulation according to claim 2 wherein the proportion of intra-granular disintegrant is 0.1 to 10 wt % of the weight of the granulate.

4. A tablet formulation according to claim 1 in which the intra-granular disintegrant is CLPVP or sodium starch glycollate, and optionally one or more diluent(s), in a proportion 70–99 wt % medicament, 1–5 wt % disintegrant and up to 30 wt % diluent.

5. A tablet formulation according to claim 1 wherein the granulate comprises 70 wt % or more of the tablet weight.

6. A tablet formulation according to claim 1 in which the extra-granular disintegrant is selected from the group consisting of maize starch, rice starch, CLPVP, sodium starch glycollate, croscarmellose sodium, microcrystalline or microfine cellulose, low-substituted hydroxypropylcellulose, cross-linked sodium carboxymethylcellulose, swellable ion exchange resins, formaldehyde-casein, and alginates.

7. A tablet formulation according to claim 1 wherein the proportion of extra-granular disintegrant in the tablet is between 0.1–25 wt % of the total tablet weight.

8. A tablet formulation according to claim 1 which contains 0–0.35 wt % lubricant.

9. The tablet formulation according to claim 1 wherein the amoxicillin is present in an amount of 375 to 1000 mg per tablet.

10. The tablet formulation according to claim 9 wherein the amoxicillin is amoxicillin trihydrate.

11. A method of treating a bacterial infection in a mammal in need thereof, which method comprises administering to said mammal, and effective amount of a formulation according to claim 1.

* * * * *